United States Patent [19]
Rose

[11] 3,976,581

[45] Aug. 24, 1976

[54] SURFACE TREATING COMPOSITIONS CONTAINING AMMONIOAMIDATE COMPOUNDS

[75] Inventor: Terence James Rose, Whitley Bay, England

[73] Assignee: The Procter & Gamble Company, Cincinnati, Ohio

[22] Filed: June 28, 1973

[21] Appl. No.: 374,589

Related U.S. Application Data

[63] Continuation-in-part of Ser. No. 243,090, April 11, 1972, abandoned.

[30] Foreign Application Priority Data

Jan. 10, 1972 United Kingdom............... 1054/72

[52] U.S. Cl................................ 252/8.8; 252/8.75; 252/117; 252/153; 252/525; 252/528; 252/544; 252/547; 252/DIG. 7; 252/DIG. 13; 252/DIG. 14; 260/561 H; 260/562 H; 424/70

[51] Int. Cl.².............. D06M 13/40; D06M 13/46; C11D 1/88

[58] Field of Search................ 252/8.75, 8.8, 544, 252/547, 525, DIG. 7, DIG. 13; 260/561 H, 562 H; 424/70

[56] References Cited

UNITED STATES PATENTS

| | | | |
|---|---|---|---|
| 3,410,880 | 11/1968 | Brocklehurst | 260/561 H X |
| 3,485,806 | 12/1969 | Bloomquist et al. | 260/561 H X |
| 3,546,115 | 12/1970 | Gill et al. | 252/8.8 |
| 3,649,569 | 3/1972 | McCarty | 252/547 X |
| 3,697,452 | 10/1972 | Olson, Jr. et al. | 252/547 X |
| 3,795,611 | 3/1974 | Wixon | 252/8.8 X |
| 3,897,348 | 7/1975 | Atkinson | 252/8.75 |

FOREIGN PATENTS OR APPLICATIONS

| | | | |
|---|---|---|---|
| 2,055,685 | 5/1972 | Germany | 252/8.8 |
| 2,213,556 | 9/1973 | Germany | 252/8.75 |
| 1,003,926 | 9/1965 | United Kingdom | 252/117 |

OTHER PUBLICATIONS

Andersen, "Ampholytic Detergents", Article in American Perfumer and Aromatics, Documentary Edition, pp. 162 and 163, Feb. 17, 1960.

*Primary Examiner*—Richard D. Lovering
*Attorney, Agent, or Firm*—Forrest L. Collins; Robert B. Aylor; Edmund F. Gebhardt

[57] ABSTRACT

Surface-treating compositions containing ammonioamidate surface-active compounds able to exist in either cationic or zwitterionic form are disclosed. The compositions which contain a buffering agent to control pH and the cationic or zwitterionic character of the ammonioamidates are effective in the treatment of fabric or hard surfaces. Hair treating compositions and processes are disclosed. Methods of treating fabric and hard surfaces to provide fabric softening and soil-release properties are also disclosed.

12 Claims, No Drawings

SURFACE TREATING COMPOSITIONS CONTAINING AMMONIOAMIDATE COMPOUNDS

CROSS-REFERENCE TO RELATED APPLICATION

This application is a continuation-in-part of the application of Terence James Rose having Ser. No. 243,090, filed Apr. 11, 1972, and now abandoned.

BACKGROUND OF THE INVENTION

This invention relates to surface-treating compositions comprising certain nitrogen ylides, ammonioamidates, which are surface-active agents and are able to exist in zwitterionic (ylide) form or in cationic form.

Quaternary ammonium compounds having at least one long chain (about $C_8$ upwards) hydrophobic radical in the molecule have long been known. They are useful as cationic surface-active agents (so called "invert soaps"), as textile softening agents and as bactericides. When intended for use as surface-active agents, the long chain group usually has from about 12 to about 20 carbon atoms. When intended for use as textile softeners, long-chained compounds, for instance having about 16 to 22 or more carbon atoms, are preferred, especially compounds possessing two long chain groups. Typical examples include: octadecyldimethyl benzyl ammonium chloride, octadecyltrimethyl ammonium chloride, distearyl dimethyl ammonium chloride, the corresponding bromides, and many others of similar structure.

These compounds, particularly distearyl dimethyl ammonium chloride, have been used commercially in textile softening compositions intended to be added to the last rinse water after a conventional washing process, and attempts have been made to use them in detergent compositions intended to be combined washing and textile softening agents.

Being cationic, these substances ordinarily react with anionic detergents to form insoluble substances, and so their use in the presence of anionic detergents is not normally practicable. Furthermore, they have a strong affinity for fabrics, especially cotton and wools, a fact which plays an important part in their effectiveness as textile softeners and bactericides, but also has the effect that they are generally not completely washed out of the fabric in a succeeding wash. They therefore tend to build up on repeatedly washed fabrics, and may thus impair the rewetting properties of the fabrics, tend to cause discoloration, fiber snagging and even cause undesirable odors.

Other quaternary ammonium compounds constitute the known zwitterionic surface-active compounds, for example, the long-chain carboxylic betaines, sulphobetaines, sulphato- and sulphito betaines. These compounds are valuable wetting agents and detergents. They are internal salts and, therefore, do not react with the metal ions present in hard water, especially calcium ions, and thus are almost unaffected by water hardness. For the same reason, they are compatible with anionic, cationic and nonionic detergents. Their affinity for and wetting effect upon certain highly hydrophobic fibers, such as polyamine and polyester fibers, renders them particularly valuable for removing certain types of soils, especially greasy soils, from these materials. They are also remarkably effective in cleaning cotton fabrics soiled with dirt which contains clay particles. However, they are not strongly substantive to fabrics and are not very effective textile softening agents. These known betaine and betaine-like compounds exist in zwitterionic form over a wide range of pH. In relatively strongly acid conditions they do become cationic, but the necessary acidity is outside the practical range for washing fabrics or human beings.

The present invention is concerned with a class of surface-active agents which are cationic under neutral or weakly acid conditions, and are zwitterionic under weakly alkaline conditions. Thus, if present at the ordinary pH of a rinsing operation in an aqueous solution (which need not, of course, necessarily in fact constitute the rinse after a wash) they are largely in cationic form and are effective as textile softening agents substantive to fabrics. Under the ordinarily alkaline conditions of a subsequent conventional washing operation, they convert to a zwitterionic form, and thus are substantially removed from the fabrics. When so removed, they are compatible with the detergent composition and may even enhance its effectiveness.

SUMMARY OF THE INVENTION

The present invention is based in part on the discovery that certain ammonioamidate surface-active compounds are particularly adapted to application to fabric or hard surfaces in a predominantly cationic and substantive form by careful control of the pH of compositions containing them and can, thereafter, by altering pH, be removed from the treated surface in a predominantly zwitterionic and relatively non-substantive form. Accordingly, in its composition aspect, the present invention provides a surface-treating composition comprising a substituted ammonioamidate having the formula:

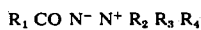

or a cationic adduct thereof having the formula:

wherein X is an anion, $R_1$ is an aliphatic, alkaryl or aromatic group containing 1 to 25 carbon atoms, $R_2$ and $R_3$ each represents a methyl, ethyl, hydroxymethyl, hydroxyethyl or cyanoethyl group, and $R_4$ is either an alkyl group having 1 to 25 carbon atoms or is a group of formula

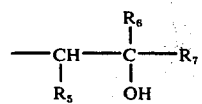

wherein $R_5$ and $R^6$ each represents hydrogen or an alkyl group with 1 to 4 carbon atoms, and $R^7$ is a group defined as $R_1$, provided that at least one of $R_1$ and $R_4$ contains an alkyl group with at least 8 carbon atoms, and a pH buffering compound.

The surface-treating compositions are suitable for treating textile surfaces such as those of fibers and fabrics, and also hard surfaces, such as those of ceramics, metals and the like.

In its process or method aspect, the present invention provides a method of treating fabric materials whereby the fabrics are improved in softness without undesirable build-up with succeeding washing treatments which comprise the steps of treating the fabrics with a solution of a predominantly cationic and fabric-substantive compound described hereinbefore thereby to improve softness, and thereafter, washing the fabrics under alkaline conditions to remove the softener in a predominantly zwitterionic form. Also provided is a method of treating hard surfaces whereby the predominantly cationic and substantive form is applied to hard surfaces, said surfaces are subjected to soiling effects and the cationic form is substantially removed by altering the pH of the treated surface to effect conversion to a predominantly zwitterionic form.

In another process aspect, the ammonioamidate is applied to hair, either in a shampoo or in a rinse or lotion, after washing with a conventional shampoo, leaving the hair glossy, easy to comb when wet or dry and acceptably free from static electricity charges which cause so-called hair "fly".

DETAILED DESCRIPTION OF THE INVENTION

The ammonioamidate compounds of the compositions of the invention can be conveniently prepared. For example, they can be prepared by alkylation of an acyl hydrazide of formula:

$R_1 CO N H N R_2 R_3$ by heating it together with either an alkyl halide wherein the halide is a chlorine, bromine or iodine atom and the remaining symbols are as defined above. The hydrazide can be prepared, for instance, by reacting an unsymmetrical dialkyl hydrazine

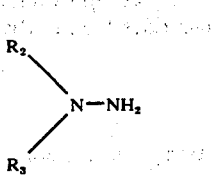

with an acyl chloride $R_1COCl$. The amidates of the invention can suitably be prepared in zwitterionic form by treating the products obtained by the above defined process with an alkali.

Acyl hydrazides can be alkylated by means of alkyl halides as is disclosed in British Patent No. 1,003,926. The compounds wherein $R^4$ is a group

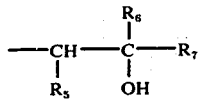

may be prepared as described in Netherlands Patent Application No. 69/01911.

The anion X, in the amidates of the invention in their cationic form, may be any convenient anion, for example halide (e.g., chloride or bromide), sulfate or methosulphate. Other anions include bisulfate, nitrate, perchlorate and fluoroborate. Often, the anion is the anion of a buffering agent with which the amidate is associated in a composition as described hereinafter.

As indicated above, the ammonioamidates must contain a group having an alkyl radical with at least 8 carbon atoms as a hydrophobic group. Optionally there may be a long chain group at both ends of the formula, i.e. as $R_1$ and as $R_4$ or $R_7$. Preferably the ammonioamidates contain a long chain group at one end and only short chain group or groups at the other. Thus preferably either $R_1$ is a long chain alkyl group having 9–21 carbon atoms, especially 15–19 carbon atoms, or an alkyl phenyl radical having 8–15 carbon atoms, especially 11–14 carbon atoms in the alkyl group. When $R^1$ is an alkyl group, $R_1CO$ becomes an acyl radical obtainable from natural or synthetic fatty acids; when $R_1$ is an alkyl phenyl group, it may be derived from the widely employed alkyl benzenes, such as the detergent alkylates, for instance commercial linear dodecyl benzene. When $R_1$ is thus long chained, $R_4$ is preferably $C_{1-4}$ alkyl, more preferably methyl or ethyl, especially methyl, or has the formula

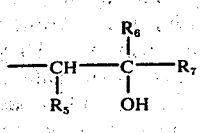

wherein $R_7$ is hydrogen or a lower alkyl group having 1 to 4 carbon atoms, or is phenyl or benzyl, but is preferably methyl or ethyl, especially methyl.

Alternatively $R_1$ may be short chained, for instance, it represents an alkyl group having 1 to 4 carbon atoms, especially 1 to 3 carbon atoms, particularly methyl or ethyl, or represents a phenyl group, and $R_4$ may be an alkyl group having 8–25 carbon atoms, preferably 16–20 carbon atoms or may be a group of formula

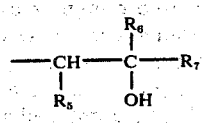

wherein $R_7$ is an alkyl group having 8–25 carbon atoms, preferably 16–20 carbon atoms or an alkyl benzyl group having 8–15 carbon atoms in the alkyl chain. When the compositions are intended for textile softening, it is particularly preferred that there should be present, in the ammonioamidate, an alkyl group with 16–20 carbon atoms or an alkyl phenyl group with at least 12 carbon atoms in the alkyl chain.

In any of these compounds, each of the groups $R_2$ and $R_3$ is preferably methyl or ethyl especially methyl, and $R_5$ and $R_6$ are preferably hydrogen.

As suitable compounds there may be mentioned particularly the compounds having the following formulae in zwitterionic (ylide) form.

$C_{15}H_{31}CON^-N^+(CH_3)_3$ $C_{17}H_{35}CON^-N^+(CH_3)_3$

$CH_3CON^-N^+(CH_3)_2CH_2CH(OH)C_{15}H_{31}$

Preferred compounds according to the invention have a pKa value in the range from 5 to 7. The pKa value is the pH at which the compounds are present 50 molar percent in zwitterionic (ylide) form and 50 percent in cationic form. At a pH below the pKa value the compounds are predominantly in cationic form, and at a pH above the pKa value they are predominantly in zwitterionic form. At pH values near the pKa value both forms are present to a considerable extent.

The compositions of the invention can comprise an amidate, as described herein, in its cationic or zwitterionic form together with suitable buffering agents, and may be intended for use in an aqueous liquor of pH less than, equal to, or not more than 2 units higher than the pKa value of the amidate. The pH buffering agent in these compositions is selected to ensure that an aqueous solution of the composition, having a concentration such that 0.1 percent by weight of said amidate is present, will have a pH in said range. Preferably the pH of the solution is within 2 units, or more preferably within 1 unit, above or below the pKa value. In solution, the amidate will then be present to a considerable extent in the form of its cationic acid adduct and will be substantive to, and adsorbed upon most surfaces to be treated. In such solutions, the anion of the cationic form of the amidate is often that of the buffering agent. Any effective buffering agent can be used, which is effective at the desired pH, for instance phosphates, polyphosphates, borates, salts of weak organic acids, such as citric, lactic, glycolic, malic, tartaric, acetic, capric, benzoic or adipic, the corresponding acids and mixtures of any of these. Preferred buffering agents are the alkali metal (e.g. sodium and potassium) phosphates, polyphosphates, borates and citrates.

The compositions of the invention can be used to treat surfaces, especially textiles, on any occasion and, in particular they are suitable as rinse additives. Thus they can be added to the rinse liquor after a surface, such as that of a textile fabric, has been washed, to provide the beneficial effects described above. Rinse additive compositions, comprising an ammonioamidate of the invention and a buffering agent effective to provide an aqueous solution of the composition with a pH which ensures the existence of the ammonioamidate in a predominantly cationic and fabric-substantive form, constitute preferred embodiments of the invention.

Suitable rinse additive compositions of the invention are exemplified as follows:

| Ingredient | Preferred (% by wt.) | Range (% by wt.) |
|---|---|---|
| Ammonioamidate | 5.25 | 1–20 |
| Buffering agent (e.g., glycolic acid) | 7 | 1–20 |
| Emulsifying agent (e.g., Butyl Carbitol) | 10 | 0–15 |
| Water | Balance to 100 | Balance to 10 |

Alternatively, the amidates can form at least part of the active organic detergent of a washing composition or liquor adapted to the washing of textile or other surfaces. A detergent composition, e.g. a conventional heavy-duty laundry detergent, containing an ammonioamidate of the invention will be formulated so that its pH in aqueous solution as used is above the pKa value of the amidate, preferably at least 2 units above it, so that the amidate will be predominantly in zwitterionic form. Thus, the buffering agent should be such that the pH of a solution of the composition, having a concentration such that there is present 0.1% by weight of the said amidate, is at least one unit, and preferably at least 2 units, above its pKa value. The amidate will then play its part in the washing action of the detergent composition, and the proportion of it present in the rinse, when dilution with tap water or the like may have reduced the pH to near its pKa value will then be converted to some degree to cationic form and be substantive to the surface being treated. However, the pKa value of these amidates being usually in the range from 5 to 7, often the pH of even a second or third rinse water remains well above the pKa value, owing to the carrying over of alkaline builders from the wash liquor. Accordingly, this method of employing the amidates as detergent-compatible textile softeners and soil release agents would be expected to be less effective than the method of adding them in a rinse or like treatment. However, it has been found to be more effective than would be expected, and, furthermore, it is often a more convenient method, especially for domestic users.

Generally it is preferred that the amidate, in cationic form, should be present in a treatment solution at a level such as to provide about 0.01 to 5 percent, for example about 0.1 percent, of said cationic form of the amidate, based on the dry weight of a fabric being treated. The concentration of amidate in a treatment solution will depend, for example, on the cloth load, but can suitably be in the range from about 0.001 to 0.5 percent, preferably from about 0.02 to 0.2 percent, by weight of the solution. Correspondingly, the proportion employed in a surface treating composition will depend on the concentration at which it is intended to be used, so as to provide the above concentrations in the working solution. As a guide, an effective composition will contain about 5 percent by weight of the amidate.

The compositions of the invention can contain compatible components commonly included in compositions of the particular type. Thus the "rinse additive" type of compositions can contain inorganic or organic salts (other than those employed as pH buffers), chelating agents, emulsifiers, solvents, coupling agents and the like, provided that they do not displace the pH from the required range. As examples there may be mentioned: sodium sulphate, sodium chloride, and organic acid salts. The detergent compositions can contain water-soluble detergency builder salts such as the inorganic phosphates, polyphosphates, silicates, carbonates or borates, and the organic alkaline sequestrants such as nitrilotriacetates, or polycarboxylates, such as those described in U.S. Pat. No. 3,308,067 (Mar. 7, 1967) including gluconates, polyitaconates, and the like. Usually the salts are the sodium salts, but other anions may be used provided that the salts are sufficiently water soluble. Some of the salts can well function both as pH buffers and builders.

In such alkaline detergent compositions, the amidate in zwitterionic form is compatible with all classes of organic detergent including anionic, nonionic and zwitterionic detergents. Most heavy duty built alkaline detergent compositions are based on anionic detergents, either soap or non-soap, and the amidates are compatible with these detergents. In soap compositions, they may act as lime-soap dispersing agents, and for this purpose are generally present at a level of about 10 to 20 percent by weight of the soap, but some effect is obtained by as little as 1 percent, and higher levels of up to at least 30 percent can be used. Suitable anionic non-soap detergents include any of those normally used in detergent compositions, such as alkyl benzene sulfonates, alkyl sulfates, alkyl ether sulfates and the like. Anionic surfaces active agents are preferably avoided in compositions containing the cationic form of the amidates, since they tend to react together to form insoluble substances. However, these insoluble substances if formed on or entrapped in a fabric do have softening properties, and they are soluble in the alkaline condition of a subsequent wash.

Suitable nonionic and zwitterionic detergents include those known in the art. As examples of the nonionics there may be mentioned: polyethylene oxide condensates of long chain fatty acids, fatty alcohols, amines, alkyl phenols and the like, polyethyleneimine condensates of fatty acids, amines or amides; polyethoxy-polypropoxy condensates such as the "Pluronics" (Trade name); and polyethoxy sorbitan esters such as the "Tweens" (Trade name). The zwitterionics include long chain alkyl or alkyl benzyl betaines; sulphobetaines, certain amino acids and the like. Other examples of suitable detergents are provided in U.S. Pat. No. 3,213,030, issued Oct. 19, 1965, lines 53–75 of column 3 lines 1 to 75 of column 4 and lines 1 to 30 of column 5, which disclosure is incorporated herein by reference. Normally, the built detergent compositions of the invention will comprise the ammonioamidate of the invention in an amount of 1 to 20 percent, preferably 10 to 20 percent, and an admixture of detergent active and builder salt as described above in a ratio of detergent to builder of from about 2:1 to about 1:10 by weight.

The compositions also cotain compatible minor ingredients of any of the types commonly used in detergent and softening compositions. These include, for example: perfumes, colors, bactericides, bleaching agents, enzymes, activators or stabilizers for them, foam-enhancing or -suppressing agents, tarnish and corrosion inhibitors, soil-suspending agents and the like.

The compositions of the invention are especially suited to the improvement of the feel or hand of treated textiles and in the treatment of other surfaces. Both on textile and like fibers and on other surfaces, for example hard surfaces, the adsorbed cationic and/or zwitterionic layer provides a surface which tends to repel important classes of soil (or dirt) and to promote their separation from the surface and their dispersion in a subsequent alkaline wash, when the adsorbed layer is rendered non-substantive. These substances can, thus, act as soil-release agents, which are removed to a considerable degree at each wash, and can be reapplied in a rinse or like treatment before the surface is re-exposed to soiling. They also provide anti-static properties for the surfaces treated with them when in their cationic form.

The compositions of the invention have a further benefit, in that they reduce the extent of wrinkling or creasing of fabrics, for instance polyester-cotton fabrics, in the wash, and/or make such wrinkle or creases as are formed more easily removed by ironing. Furthermore, they have a lubricating effect so that there is less frictional resistance to the movement of an iron. Thus the effort of ironing garments treated with these compositions is appreciably lessened.

The compositions are also suitable for treating hard surfaces so as to facilitate cleaning them. By "hard surfaces" are meant principally those exposed to air-borne soiling, such as windows, whether of buildings or of vehicles, motor bodies and metal trim, paintwork, stone or brick work, domestic furniture especially sanitary were and cookers and the like. The invention is also applicable to crockery, plate and cutlery and the like.

These surfaces often become soiled by air-borne dust, by spray and splashing, for instance on roads or by deposits from smoke and fumes or the like. These soil deposits usually contain grease, as for example, soot, deposits from motor exhaust or cooking fumes. They also often contain clay or like particles for example from wind-borne dust and road spray. Generally, they adhere quite strongly to most surfaces so that the surfaces must be rubbed, preferably in the presence of detergents or wetting agents, in order to clean them. Treatment with the compositions of the invention renders such surfaces easier to clean, so that if they are sprayed or flushed with water, the adherent soil deposits are mostly carried away without rubbing. Alternatively, surfaces which cannot conveniently be sprayed or flushed with water can be cleaned with a cloth wet with water, with a minimum of rubbing.

The compositions also render the treated surfaces to some degree antistatic reducing the tendency for dust to adhere to them. They also render windows and like surfaces less liable to condensation of moisture and misting.

The hair treating compositions of this invention include shampoos, and compositions intended to be applied after shampooing, e.g., lotions or rinses. Any effective proportion of the ammonioamidates of this invention can be used in the hair shampooing and conditioning compositions of the invention, together with such conventional components as are desirable to make the product easy to apply and attractive. Usually shampoo compositions and rinses are liquids intended to be applied in concentrated form to the wetted hair. In such compositions, generally from about 0.01 to about 5 percent or more by weight of ammonioamidate is suitable. At a concentration of over about 5 percent, aqueous solutions of the ammonioamidate in nearly neutral solutions which are appropriate for shampoos and the like, may become gelatinous and special precautions or other additives may be necessary to overcome this. As will be understood, quite different proportions would be suitable in compositions intended to be diluted before use.

In addition to the ammonioamidates, the shampoo compositions of this invention can contain organic water-soluble, non-soap, non-cationic surfactants. Cationic surfactants are generally avoided in shampoo compositions because they have little cleaning power on hair and are liable to be harmful to the eyes. The preferred detergents used are anionic detergents of any of the classes which are suitable per se for shampoos such as alkyl sulfate, alkyl ether sulfates, alkyl glyceryl ether sylfonates, sulfosuccinates, and others known in the art containing an alkyl or acyl group having from about 8 to about 18 carbon atoms. These detergents are normally used in the form of their alkali metal, e.g., sodium or potassium, ammonium and substituted ammonium, e.g., triethanolammonium, diethanolammonium and monoethanolammonium salts. The surfactants can be present in the usual concentrations, e.g., from about 5 to about 60 percent by weight of the composition, generally from about 20 to about 40 percent by weight of the composition in liquid shampoos.

The anionic detergents can be replaced by nonionic, ampholytic, or zwitterionic detergents, or any of these may be present in addition to the anionic detergent. Examples of these detergents may be selected from types known in the art to be suitable for shampoo formulations. Suitable detergents are listed in "Formulation and Function of Cosmetics", J. S. Jellinek, published by Wiley & Sons, 1970, pp. 230–240; and in U.S. Pat. Nos. 3,400,198; 3,580,853, 3,549,542; 3,549,546;

3,313,734; and 3,400,198, said patents being incorporated herein by reference.

The proportion of the ammonioamidates in liquid shampoo compositions can be within the range stated above but is preferably in the upper part of the range, e.g., from about 1 to about 3 percent by weight. It is believed that the ammonioamidates are strongly adsorbed on the keratin of the hair, but that some small degree of desorption may taken place during the several rinses to which the hair is subjected after shampooing. The proportion of the ammonioamidate should be high enough to ensure that an effective amount remains on the hair after rinsing.

In addition to a main detergent active compound as referred to above and the ammonioamidate, the shampoo compositions can also contain other ingredients usual in shampoos such as one or more of the following substances: Suds boosters, such as fatty acid amides; emollients, such as lanolin and lecithin; bacteriostats; bactericides; preservatives; dandruff controlling agents such as zinc 2-pyridinethiol-1-oxide; opacifiers, e.g., polyethylene glycol distearate; viscosity controlling agents such as carboxymethylcellulose, alginates, etc.; resins, etc., to impart gloss to the hair; a liquid solvent or dispersing medium, e.g., water, lower alcohol, glycerol, etc.; hormone products; optical brighteners; perfume; colorant matter; etc. Preferred ingredients include bactericides, dandruff control agents, suds boosters and stabilizers, viscosity controllers, opacifiers, preservatives, color, and perfume.

The present invention also includes a method of treating hair which comprises applying thereto a composition as defined above.

The following Examples illustrate the invention:

EXAMPLE I

Cotton terry towels were given a preliminary wash in a 0.5 percent by weight solution of a typical heavy duty household bleach, with perborate, and detergent composition, in tap water (hardness 170 parts per million as Ca CO$_3$), at 43°C for 5 minutes. After rinsing, the towels were treated with one of the following solutions, rinsed again and dried.

The solutions were:
a. a commercial textile softening composition based on ditallowyldimethyl ammonium chloride at a concentration corresponding to 0.1% by weight of the cationic surfactant,
b. a solution of pH 5.5 containing citric acid and 0.1 percent by weight of hexadecylamide-trimethylammoniumiodide,
c. tap water.

The towels were then soiled with a natural composite soil containing clay and carbon particles and greasy components, obtained by rubbing motor car windscreens and hub caps. The towels were then washed again and treated with the same solution as before.

After this first cycle, the cloths treated in solutions (a) and (b) were equally soft to handle, and softer than those treated in solution (c).

The towels were resoiled and washed in fresh detergent and treated in fresh solutions of the same kind as before. After 10 such cycles, the following comparisons were observed.

Softness (by feel)
Solution (a) equal to Solution (b) better than Solution (c).

Whiteness (visual examination)
Solution (b) better than Solution (c) better than Solution (a).

It was further observed that the softness after 10 cycles in solution (b) was about equal to that after 1 cycle in solution (b) or one cyle in solution (a), and that the towels after 10 treatments in solution (a), though softer than those treated in solution (b), had an unpleasant greasy feel. Thus the method of the invention, that using solution (b), provided textile softening without undesirable build up and greasiness, and also promoted improved cleaning.

Substantially the same results are obtained when hexadecylamide-dimethyl-2-hydroxypropyl ammonium chloride replaces hexadecylamide-trimethylammonium iodide in this example.

EXAMPLE II

Ironing Ease

Cotton and polyester/cotton handkerchiefs were washed at 140°F in a 0.1 percent solution of an anionic detergent-based commercial heavy duty household washing composition ("Cheer" — Procter and Gamble) for 10 minutes, rinsed in water at 105°F for 10 minutes, spin-dried and tumble-dried at 140°F for 20 minutes. Both the wash and rinses used a 20/1 ratio of water to dry fabric by weight. The rinse water for reference fabrics contained no additives other than the 7 gr/gal. hardness present in all wash and rinse solutions. The treatment rinses contained varying amounts of ammonioamidate or a quaternary ammonium compound as indicated below. Ease of ironing was determined by a measurement of the frictional force within the fabric and between fabric and iron using a modified Instrom tensile strength apparatus. Ironing was continued to an end point of removal of wrinkles from the fabrics.

The following compounds were tested — (a) distearyl dimethyl ammonium chloride; (b) $C_{15}H_{31}CON^-N^+(CH_3)_2CH_2CH(OH)CH_3$.

The ironing effort values relative to water rinsed cotton at a value of 100 and water rinsed polyester/cotton blend at a value of 63 were:

| | Relative Ironing Effort | | | | | |
|---|---|---|---|---|---|---|
| Gms Active/Kg. Fabric | 0.5 | | 1.0 | | 2.0 | |
| | cotton | (blend)* | cotton | (blend)* | cotton | (blend) |
| Quaternary a | 80 | 48 | 60 | 55 | 50 | 45 |
| Ylide b | 70 | 32 | 52 | 30 | 40 | 30 |

*(65/35 blend of Polyester/Cotton with permanent press finish)

EXAMPLE III

Pieces of cotton terry towelling are given a 10 minute wash at 50°C in solutions as indicated below in 18° hard water. They are then squeezed out, given two 1-minute rinses in cold water (18° Hard), squeezed and dried in the open air. Their softness is then evaluated by a paired comparison method by a panel of six ladies.

Compositions of wash liquors are:
a. Conventional heavy duty detergent 0.55%,
b. Solution (a) with the addition of 0.08% of the compound $C_{15}H_{31}CON^-N^+(CH_3)_2CH_2CH(OH)CH_3$,
c. Solution (a) with the addition of 0.08% of the compound $C_{15}H_{35}CON^-N^+(CH_3)_3$.

The fabrics washed with Solutions (b) and (c) are noticeably softer than those washed with Solution (a).

EXAMPLE IV

Six swatches of human hair were given a standard preliminary wash in an unbuilt detergent composition based on mixed sodium alkyl benzene sulfonate and sodium alkyl ether sulfate active detergents. The treatment comprised a wash, water rinse, second wash and rinse followed by air drying. The swatches were then treated as follows:

i. Six swatches were wetted for 5 seconds in running (10 liter/minute) 2°H. water at 40°C (105°F).
ii. Each swatch as lathered by hand in commercial shampoo (2 ml).
iii. Each swatch was rinsed for 15 seconds in 2°H. running water (10 liter/minute) at 40°C. (105°F).
iv. Repeat of (ii).
v. Three of the swatches were rinsed in water as in (iii).
vi. The other three swatches were rinsed for 15 seconds in 0.02 percent solution (1 liter) of ammonioamidate, buffered with sodium citrate/citric acid to pH 6.5, the proportions of amidate citrate and citric acid being 5:2:3 by weight.
vii. Each swatch was air-dried.

AMMONIOAMIDEATES USED

A-$C_{16}$ hydroxypropyl ylide adduct $(C_{15}H_{31}CO\ NH\ N(CH_3)_2CH_2CHOHCH_3)^+\ Cl^-$ B-$C_{16}$ trimethyl ylide adduct $(C_{15}H_{31}CO\ NH\ N(CH_3)_3)^+\ Cl^-$

RESULTS

The gloss and softness of the treated swatches were evaluated by a panel of ladies using a paired comparison technique. The results are given below in panel score units (psu), with confidence limits based upon the variability of judgments of the same comparisons.

|  | Ylide adduct A | | Ylide adduct B | |
|---|---|---|---|---|
|  | Gloss | Softness | Gloss | Softness |
| Water rinse treatment mean | −0.53 psu | −0.30 psu | −0.57 psu | −0.66 psu |
| Ammonioamidate rinse treatment mean | +0.54 psu | +0.31 psu | +0.58 psu | +0.67 psu |
| Difference in treatment mean | 1.07 psu | 0.61 psu | 1.15 psu | 1.33 psu |
| 95% confidence interval | 0.84 psu | 0.42 psu | 0.84 psu | 1.02 psu |

Commercial Shampoo Formulation

| | |
|---|---|
| Triethanolamine alkyl sulfate | 55% |
| Triethanolamine | 2 |
| Coconut monoethanolamide | 4 |
| Water and miscellaneous | 39 |
| | 100 |

EXAMPLE V

When in the above examples the following ammonioamidates are substituted either wholly or in part, e.g., 1:1 ratios, for the specifically named ammonioamidates, being added in the zwitterionic or cationic (chloride, bromide, phosphate, citrate, etc.), form as is appropriate, substantially equivalent results are obtained in that the surfaces are conditioned:

$C_{17}H_{35}CON^-N^+(CH_3)_3$;

$C_{17}H_{35}CON^-N^+(CH_3)_2CH_2CH(OH)CH_3$;

$CH_3CON^-N^+(CH_3)_2CH_2CH(OH)C_{15}H_{31}$;

$C_{12}H_{25}C_6H_4CON^-N^+(CH_3)_3$;

$C_{19}H_{39}CON^-N^+[C_2H_4(OH)]_3$;

$C_{17}H_{35}CON^-N^+(C_2H)_2C_4H_9$;

$C_{17}H_{35}CON^-N^+[CH_2(OH)]_2CH_2CH(OH)C_{17}H_{35}$;

$C_2H_5CON^-N^+(CH_3)_2CH_2CH(OH)C_6H_4C_{12}H_{25}$;

$C_2H_5CON^-N^+(CH_3)_2CH(CH_3)C(CH_3)(OH)C_{18}H_{37}$; and $C_{17}H_{35}CON^-N^+(C_2H_4CN)_2CH_3$.

What is claimed is:

1. A surface-treating composition suitable for hair and fabric softening consisting essentially of:
   a. a substituted ammonioamidate having the formula

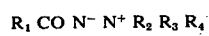

or a cationic adduct thereof having the formula

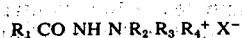

wherein X is an anion; $R_1$ is an alkyl, phenyl, or alkylphenyl group having 1 to 25 carbon atoms; each of $R_2$ and $R_3$ is a methyl, ethyl, hydroxymethyl, hydroxyethyl or cyanoethyl group; and $R_4$ is either an alkyl having 1 to 25 carbon atoms or:

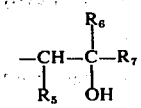

wherein each of $R_5$ and $R_6$ is a hydrogen or an alkyl group with 1 to 4 carbon atoms, and $R_7$ is a group defined as $R_1$, benzyl or hydrogen, provided that at least one of $R_1$ and $R_4$ contains an alkyl group with at least 8 carbon atoms, said compound having a pKa value of from about 5 to about 7; and b. a pH buffering compound selected from the group consisting of:
   i. the alkali metal acid salts of phosphoric acid, and the polyphosphoric acids;
   ii. the acids and corresponding alkali metal salts of weak organic acids, and;
   iii. boric acid and borates;

or mixtures thereof in an amount sufficient to maintain the pH of a solution containing component (a) at a level of from about 0.001 to about 0.5 percent by weight at less than, equal to, or not greater than 2 pH units above the pKa of component (a).

2. The composition of claim 1 wherein $R_1$ is an alkyl group having 9 to 21 carbon atoms or an alkyl phenyl group having 8 to 15 carbon atoms in the alkyl chain, and $R_4$ is an alkyl group having 1 to 4 carbon atoms, or

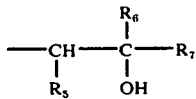

wherein $R_7$ is an alkyl group having 1 to 4 carbon atoms, a phenyl or benzyl group or hydrogen.

3. The composition of claim 2 wherein $R_1$ is an alkyl group having 15-19 carbon atoms.

4. The composition of claim 3 wherein $R_4$ is methyl or ethyl or

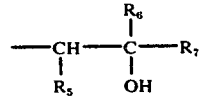

wherein $R_7$ is methyl or ethyl.

5. The composition of claim 1 wherein $R_1$ is an alkyl group having 1 to 4 carbon atoms or a phenyl group and $R_4$ is an alkyl group having 8-25 carbon atoms, or

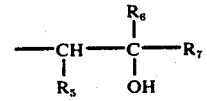

wherein $R_7$ is an alkyl group having 8-25 carbon atoms or an alkyl benzyl group having 8-15 carbon atoms in the alkyl chain.

6. The composition of claim 5 wherein the group $R_4$ is an alkyl group having 16-20 carbon atoms, or

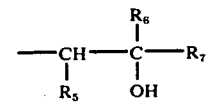

wherein $R_7$ is an alkyl group having 16-20 carbon atoms.

7. The composition of claim 6 wherein $R_1$ is methyl or ethyl.

8. The composition of claim 7 wherein each of $R_2$ and $R_3$ is a methyl or ethyl group.

9. The composition of claim 8 wherein $R_5$ and $R_6$ if present, are each a hydrogen atom.

10. The composition of claim 1 wherein said buffering compounds are selected from the group consisting of water-soluble citrates and borates, the corresponding acids and mixtures thereof.

11. The composition of claim 10 which which also contains one or more nonionic or zwitterionic surface active agents.

12. A fabric softening composition consisting essentially of:

a. a substituted ammonioamidate having the formula

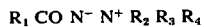

or a cationic adduct thereof having the formula

wherein X is an anion; $R_1$ is an alkyl, phenyl, or alkylphenyl group having 1 to 25 carbon atoms; each of $R_2$ and $R_3$ is a methyl, ethyl, hydroxymethyl, hydroxyethyl or cyanoethyl group; and $R_4$ is either an alkyl having 1 to 25 carbon atoms or:

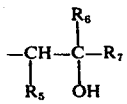

wherein each of $R_5$ and $R_6$ is a hydrogen or an alkyl group with 1 to 4 carbon atoms, and $R_7$ is a group defined as $R_1$, provided that at least one of $R_1$ and $R_4$ contains an alkyl group with at least 8 carbon atoms, said compound having a pKa value of from about 5 to about 7; and b. a pH buffering compound selected from the group consisting of the acids and corresponding alkali metal salts of citric acid, lactic acid, glycolic acid, malic acid, tartaric acid, acetic acid, capric acid, benzoic acid, and adipic acid;

or mixtures thereof wherein the buffering compound is present in amount sufficient to maintain the pH of a solution containing component (a) at a level of from about 0.02 to about 0.2 percent by weight at less than, equal to, or not greater than 2 pH units above the pKa of component (a).

* * * * *